United States Patent
George et al.

(10) Patent No.: US 8,602,722 B2
(45) Date of Patent: Dec. 10, 2013

(54) SYSTEM AND METHOD FOR INSPECTION OF STATOR VANES

(75) Inventors: Sheri George, Bangalore (IN); Vinay Bhaskar Jammu, Bangalore (IN); Vinod Padmanabhan Kumar, Bangalore (IN); Chayan Mitra, Bangalore (IN); Kunal Ravindra Goray, Bangalore (IN); Achalesh Kumar Pandey, Greenville, SC (US); Ravi Yoganatha Babu, Bangalore (IN); Bhasker Rao Keely, Bangalore (IN); Munish Vishwas Inamdar, Bangalore (IN)

(73) Assignee: General Electric Company, Niskayuna, NY (US)

( * ) Notice: Subject to any disclaimer, the term of this patent is extended or adjusted under 35 U.S.C. 154(b) by 959 days.

(21) Appl. No.: 12/714,207

(22) Filed: Feb. 26, 2010

(65) Prior Publication Data
US 2011/0211940 A1    Sep. 1, 2011

(51) Int. Cl.
*F01D 25/00*  (2006.01)

(52) U.S. Cl.
USPC .................................................. 415/118

(58) Field of Classification Search
USPC ............... 415/118, 121.3, 232; 416/5, 61, 62
See application file for complete search history.

(56) References Cited

U.S. PATENT DOCUMENTS

| 4,686,972 A | 8/1987 | Kurland |
| 4,777,949 A | 10/1988 | Perlin |
| 4,882,667 A | 11/1989 | Skegin |
| 4,991,068 A | 2/1991 | Mickey |
| 5,052,803 A * | 10/1991 | Krauter ................ 356/241.4 |
| 5,066,122 A * | 11/1991 | Krauter ................ 356/241.4 |
| 5,221,130 A | 6/1993 | Satoh et al. |
| 5,511,567 A | 4/1996 | Cefis |
| 5,560,087 A | 10/1996 | Marques |
| 5,580,159 A | 12/1996 | Liu |
| 5,627,904 A | 5/1997 | Yang et al. |
| 5,629,577 A | 5/1997 | Polla et al. |
| 5,901,896 A | 5/1999 | Gal |
| 6,126,775 A | 10/2000 | Cullen et al. |
| 6,414,458 B1 | 7/2002 | Hatley et al. |
| 6,475,188 B1 | 11/2002 | Baxter |
| 6,539,136 B1 | 3/2003 | Dianov et al. |
| 6,592,043 B1 | 7/2003 | Britton |
| 6,610,030 B1 | 8/2003 | Baxter |

(Continued)

FOREIGN PATENT DOCUMENTS

| DE | 3312987 | 10/1984 |
| DE | 4126724 | 2/1993 |

(Continued)

*Primary Examiner* — Edward Look
*Assistant Examiner* — Liam McDowell
(74) *Attorney, Agent, or Firm* — Ann M. Agosti

(57) ABSTRACT

Embodiments of the invention include an inspection system to inspect internal components of a compressor of a gas turbine engine. The inspection system includes an image recording assembly having one or more image recording devices, light sources, storage devices, and power supplies. The image recording assembly may be inserted into a compressor without removal of the compressor housing or disassembly of the compressor. The image recording assembly may be removably coupled to a rotary component of the compressor, e.g., a rotor blade, and used to record images of stationary components, e.g., stator vanes, of the compressor. The images may be inspected to identify wear and/or defects in the stationary components, e.g., stator vanes.

20 Claims, 7 Drawing Sheets

(56) References Cited

U.S. PATENT DOCUMENTS

| | | |
|---|---|---|
| 6,637,737 B1 | 10/2003 | Beecherl et al. |
| 6,992,315 B2 * | 1/2006 | Twerdochlib ............ 250/559.08 |
| 7,004,957 B1 | 2/2006 | Dampney et al. |
| 7,032,279 B2 | 4/2006 | McCarvill et al. |
| 7,075,296 B2 * | 7/2006 | Moore ........................ 324/262 |
| 7,272,253 B2 * | 9/2007 | Katsuta et al. ................ 382/141 |
| 7,489,811 B2 | 2/2009 | Brummel et al. |
| 2002/0015557 A1 | 2/2002 | Yap et al. |
| 2003/0228098 A1 | 12/2003 | Sidorovich |
| 2005/0056953 A1 | 3/2005 | Hofmann et al. |
| 2006/0234901 A1 | 10/2006 | Scheuing et al. |
| 2006/0243302 A1 | 11/2006 | Mardero et al. |
| 2007/0068995 A1 | 3/2007 | Kley |
| 2009/0240280 A1 | 9/2009 | Wang et al. |
| 2009/0278924 A1 * | 11/2009 | Heyworth et al. ............. 348/82 |
| 2009/0301055 A1 * | 12/2009 | Kallappa .................... 60/39.091 |

FOREIGN PATENT DOCUMENTS

| | | |
|---|---|---|
| DE | 19859952 | 2/2000 |
| DE | 20307024 | 8/2003 |
| DE | 10255348 | 11/2003 |
| DE | 04006503 | 9/2004 |
| DE | 06003427 | 9/2006 |
| EP | 335126 | 3/1989 |
| EP | 943916 | 9/1990 |
| EP | 432743 | 12/1990 |
| EP | 1251164 | 4/2002 |
| EP | 1747835 | 7/2005 |
| JP | 56114612 | 2/1980 |
| JP | 56135087 | 3/1980 |
| JP | 57160362 | 3/1981 |
| JP | 58146765 | 2/1982 |
| JP | 4203510 | 12/1987 |
| JP | 63132108 | 6/1988 |
| JP | 2084312 | 7/1988 |
| JP | 2130772 | 11/1988 |
| JP | 2179364 | 12/1988 |
| JP | 3113785 | 9/1989 |
| JP | 3172605 | 12/1989 |
| JP | 2163604 | 6/1990 |
| JP | 4041214 | 6/1990 |
| JP | 5026965 | 7/1991 |
| JP | 5083852 | 9/1991 |
| JP | 5084765 | 9/1991 |
| JP | 5169454 | 12/1991 |
| JP | 5192855 | 1/1992 |
| JP | 5277585 | 3/1992 |
| JP | 4294116 | 10/1992 |
| JP | 6165511 | 11/1992 |
| JP | 6226705 | 2/1993 |
| JP | 7156032 | 12/1993 |
| JP | 8303477 | 5/1995 |
| JP | 8326726 | 5/1995 |
| JP | 9047805 | 8/1995 |
| JP | 9089904 | 9/1995 |
| JP | 9310343 | 5/1996 |
| JP | 9145340 | 6/1997 |
| JP | 1228743 | 3/1998 |
| JP | 11320204 | 5/1998 |
| JP | 2000176763 | 12/1998 |
| JP | 2001162472 | 12/1999 |
| JP | 2002260711 | 2/2001 |
| JP | 2004140202 | 10/2002 |
| JP | 2004195855 | 12/2002 |
| JP | 2005285307 | 3/2004 |
| JP | 2005320749 | 5/2004 |
| JP | 2005326357 | 5/2004 |
| JP | 2007296987 | 5/2006 |
| JP | 2009139199 | 12/2007 |
| JP | 2008184871 | 1/2008 |
| WO | WO9325991 | 12/1993 |
| WO | WO9529427 | 11/1995 |
| WO | WO2004044420 | 5/2004 |
| WO | WO2007017692 | 2/2007 |
| WO | WO2009076942 | 6/2009 |
| WO | WO2009109288 | 9/2009 |

\* cited by examiner

SYSTEM AND METHOD FOR INSPECTION OF STATOR VANES

BACKGROUND OF THE INVENTION

The subject matter disclosed herein relates to gas turbine engines and, more particularly, to inspection of interior components of such turbine engines.

In general, gas turbine engines combust a mixture of compressed air and fuel to produce hot combustion gases. The combustion gases may flow through one or more turbine stages to generate power for a load and/or a compressor. The compressor may include rotary components, such as rotors and blades that rotate about a shaft, and stationary components, such as stator vanes. Over time, the various components of the compressor of the gas turbine engine may wear or develop defects. Inspection of these components to determine wear and/or defects may be difficult due to the enclosure of the gas turbine engine.

One technique for inspecting internal components of the gas turbine engine may include inserting a borescope through borescope holes to manually inspect different components, such as rotor blades or stator vanes. Unfortunately, such inspections using a borescope are time consuming and labor intensive. Additionally, the field of view of the borescope is limited and may not provide complete inspection coverage of all internal components of the gas turbine engine. Further, the borescope lens may have limitations in the depth of field and resolution, thus making interpretations and qualification of the borescope images difficult and ambiguous. Other inspection procedures may require removal of the compressor housing and disassembly of the compressor to inspect internal components.

BRIEF DESCRIPTION OF THE INVENTION

In one embodiment, a method includes rotating an image recording assembly removably coupled to a rotary component of a compressor of a gas turbine engine around a shaft of the gas turbine engine and recording images of stationary components disposed circumferentially around the shaft, without removal of a housing of the compressor.

In another embodiment, a system includes an image recording assembly for a compressor of a gas turbine. The image recording assembly includes an image recording device, a light source, a storage device and a coupling mechanism. The coupling mechanism couples the image recording system to a rotor blade of the compressor and the image recording device is oriented to record images of stator vanes of the compressor as the rotor blade rotates.

In another embodiment, a method includes inserting an image recording assembly into a compressor housing of a gas turbine engine, coupling the image recording assembly to a rotor blade of a compressor of the gas turbine engine, and determining defects in an internal component of the compressor from images recorded by the image recording assembly.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Embodiments of the invention include an inspection system to inspect internal components of a compressor of a gas turbine engine. The inspection system includes an image recording assembly having one or more image recording devices, light sources, storage devices, and power supplies. The image recording assembly may be inserted into a compressor without removal of the compressor housing or disassembly of the compressor. The image recording assembly may be removably coupled to a rotary component of the compressor, e.g., a rotor blade, and used to record images of stationary components, e.g., stator vanes, of the compressor. The image recording assembly may be removed from the compressor and the images may be provided to an image processing system for processing. The images may be inspected to identify wear and/or defects in the stationary components, e.g., stator vanes.

Figure 1:
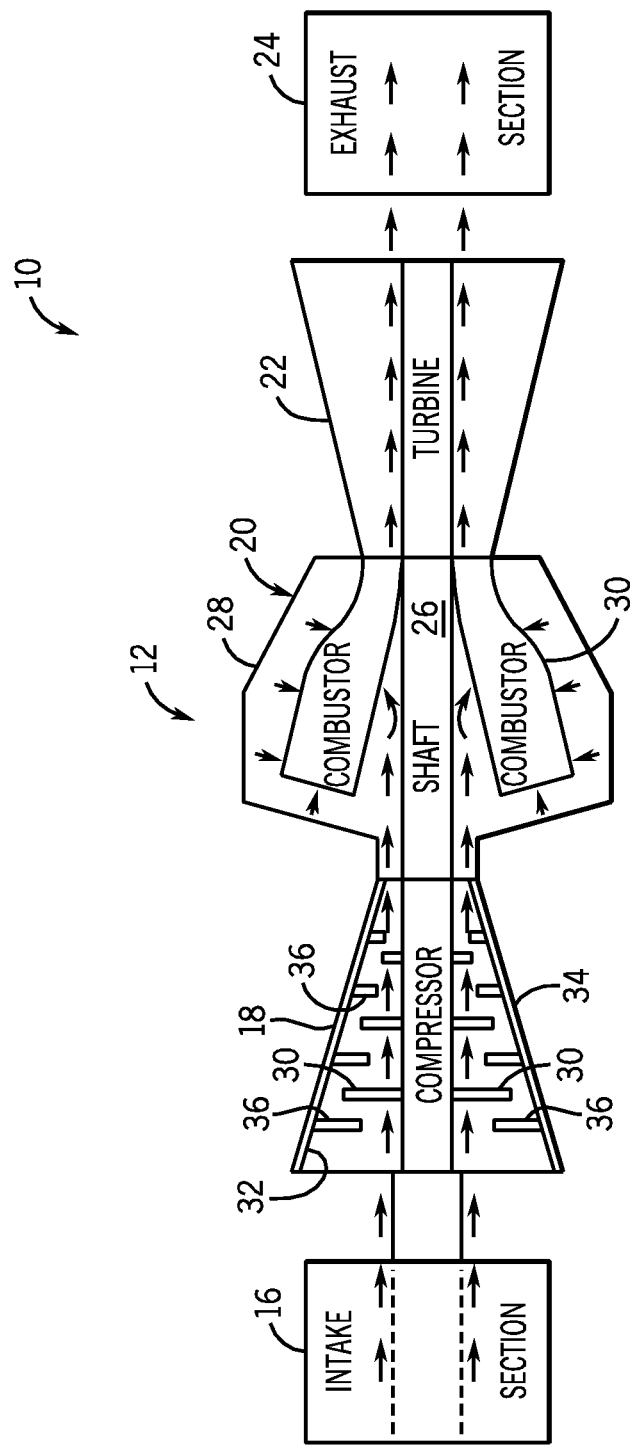
FIG. 1 is a schematic flow diagram of a gas turbine engine that may be inspected in accordance with an embodiment of the present invention.

FIG. 1 is a block diagram of an exemplary system 10 including a gas turbine engine 12 that may be inspected using the inspection system described herein. In certain embodiments, the system 10 may include an aircraft, a watercraft, a locomotive, a power generation system, or combinations thereof. The illustrated gas turbine engine 12 includes an air intake section 16, a compressor 18, a combustor section 20, a turbine 22, and an exhaust section 24. The turbine 22 is coupled to the compressor 18 via a shaft 26.

As indicated by the arrows, air may enter the gas turbine engine 12 through the intake section 16 and flow into the compressor 18, which compresses the air prior to entry into the combustor section 20. The illustrated combustor section 20 includes a combustor housing 28 disposed concentrically or annularly about the shaft 26 between the compressor 18 and the turbine 22. The compressed air from the compressor 18 enters combustors 29 where the compressed air may mix and combust with fuel within the combustors 29 to drive the turbine 22. The combustion of the air and fuel may generate hot pressurized exhaust gases, which may then be utilized to drive one or more turbine blades within the turbine.

The compressor 18 may include rotor blades 30 coupled to the shaft 26. The compressor blades 30 may span the radial gap between the shaft 26 and an inner wall or surface 32 of a compressor housing 34 in which the internal components of the compressor are disposed. As used herein, the term rotor blades 30 may also refer to "rotor buckets," e.g., the rotor blade and various components. The compressor 18 may include a rotor that couples each of the rotor blades 30 to the shaft 26. The compressor 18 may include stationary components, e.g., stator vanes 36, extending from the inner wall or surface 32 and axially offset from and adjacent to the rotor blades 30. The rotation of the shaft 26 causes rotation of the rotor blades 30, thereby drawing air into the compressor 18 and compressing the air prior to entry into the combustor section 20.

Figure 2:
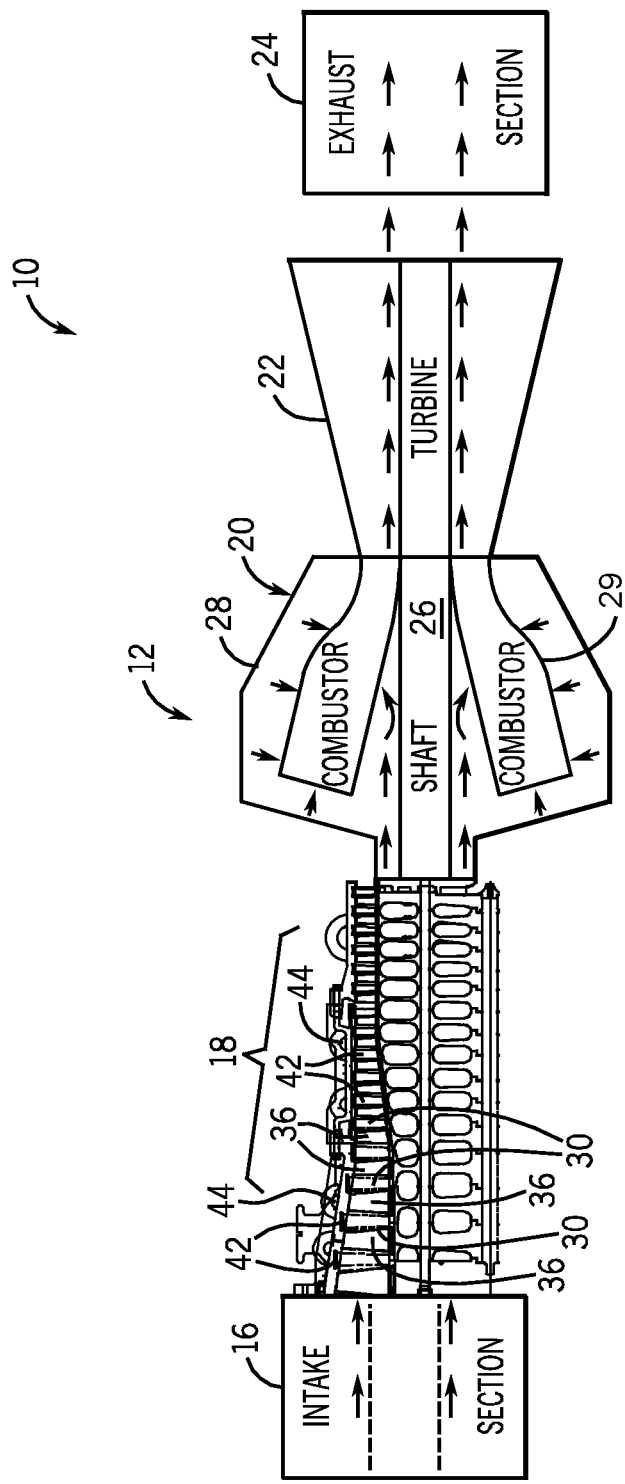
FIG. 2 is a sectional view of the compressor of the gas turbine engine of FIG. 1 sectioned through the longitudinal axis in accordance with an embodiment of the present invention.

FIG. 2 is a sectional view of the compressor 18 of the gas turbine engine 12 of FIG. 1 taken along the longitudinal axis. As depicted, the compressor 18 may include multiple rotary stages 42. Each stage may include rotary components, such as a rotor blades 30 coupled to a rotor that may be rotatably attached to the shaft 26 (FIG. 1). The blades 30 may extend radially outward from the rotor and may be partially disposed within the path of the gases and between concentric portions of stator vanes 36. The stator vanes 36 may be arranged in a circumference around the shaft 26.

As described above with respect to FIG. 1, air may enter through the air intake section 16 and be compressed by the compressor 18. The compressed air from the compressor 18 may then be directed into the combustor section 20 where the compressed air may be mixed with fuel gas. The mixture of compressed air and fuel gas is generally burned within the combustor section 20 to generate high-temperature, high-pressure combustion gases, which may be used to generate torque within the turbine 22.

During operation of the gas turbine engine 12, internal components of the compressor 18 may develop wear and/or defects. For example, the stator vanes 36 may gradually wear or develop defects that affect efficiency and output of the compressor 18. Such wear and defects may include, for example, cracks, corrosion, erosion, chipping, etc. In some embodiments, the gas turbine engine 12 may include borescope holes 44 disposed longitudinally along the compressor housing 34. The borescope holes 44 may provide for conventional inspection of interior components via a borescope. A borescope may be inserted into one of the borescope holes 44, through the housing 34 and the inner wall 32 of the compressor 18, to examine the stator vanes 36 and other internal components of the compressor 18. As described further below, the borescope holes 44 may provide access for an image recording assembly installed on the rotor blades 30 and used to record images of the stator vanes 36.

Figure 3:
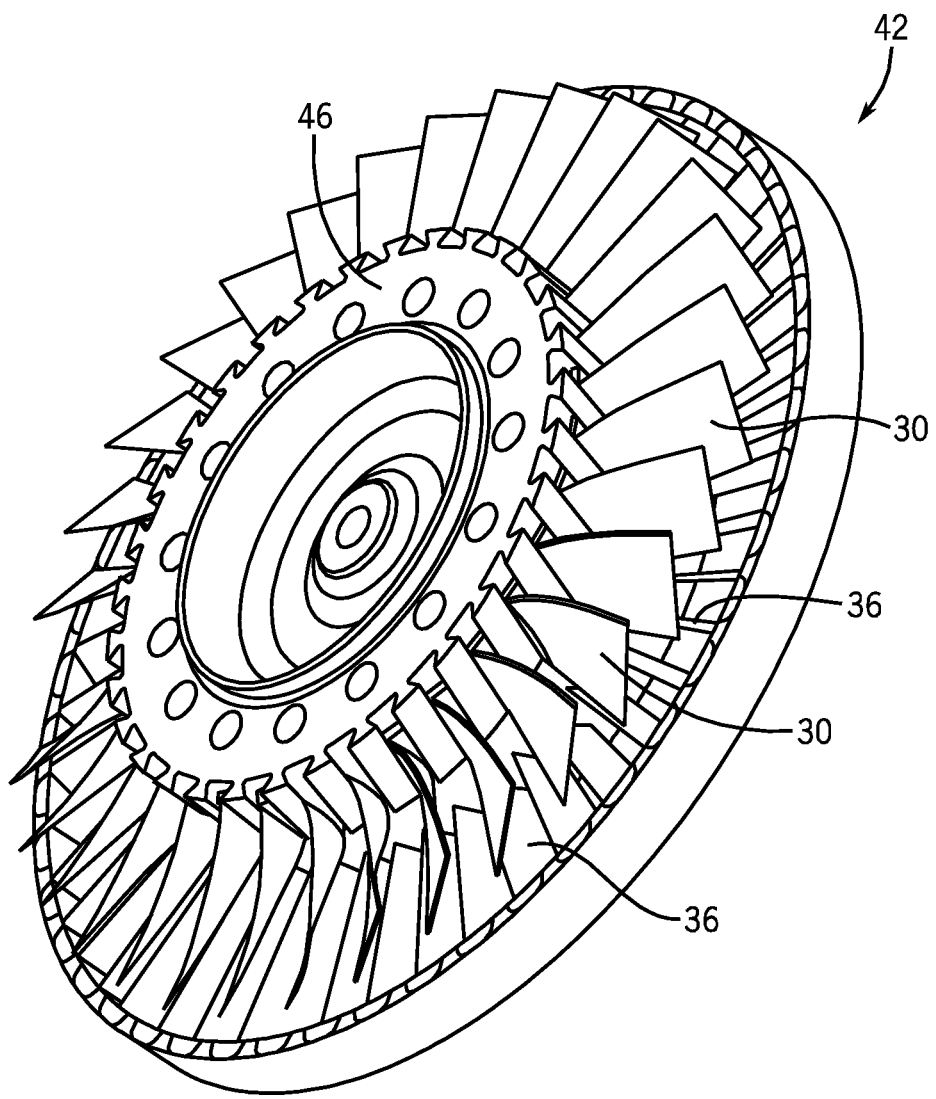
FIG. 3 is a perspective view of a stage of the compressor of the gas turbine engine of FIG. 1 in accordance with an embodiment of the present invention.

FIG. 3 is a perspective view of a stage 42 of the compressor 18. FIG. 3 further illustrates the stage 42 having a rotor 46 with rotor blades 30 extending radially therefrom. The stage 42 also shows the stator vanes 36 axially offset from and adjacent to the rotor blades 30 and extending radially toward the axis of rotation of the rotor 46. As seen in FIG. 3, the stator vanes 36 extend circumferentially around the axis of rotation of the rotor 46. As described below, embodiments of the present invention include image recording assemblies that may be secured to one or more rotor blades 30 of the compressor 18. The image recording assembly is secured to a rotor blade 30 and oriented to record images of the stator vanes 36. Additionally, image recording assemblies may be removably coupled to rotor blades on the other side of the stator vanes 36 to provide further coverage of the stator vanes 36. In other embodiments, image recording assemblies may be coupled to the space between rotor blades. As the rotor 46 rotates, the image recording assemblies also rotate around the axis of rotation, enabling the image recording device to record images of substantially all of the stator vanes 36 of the stage 42.

Figure 4:
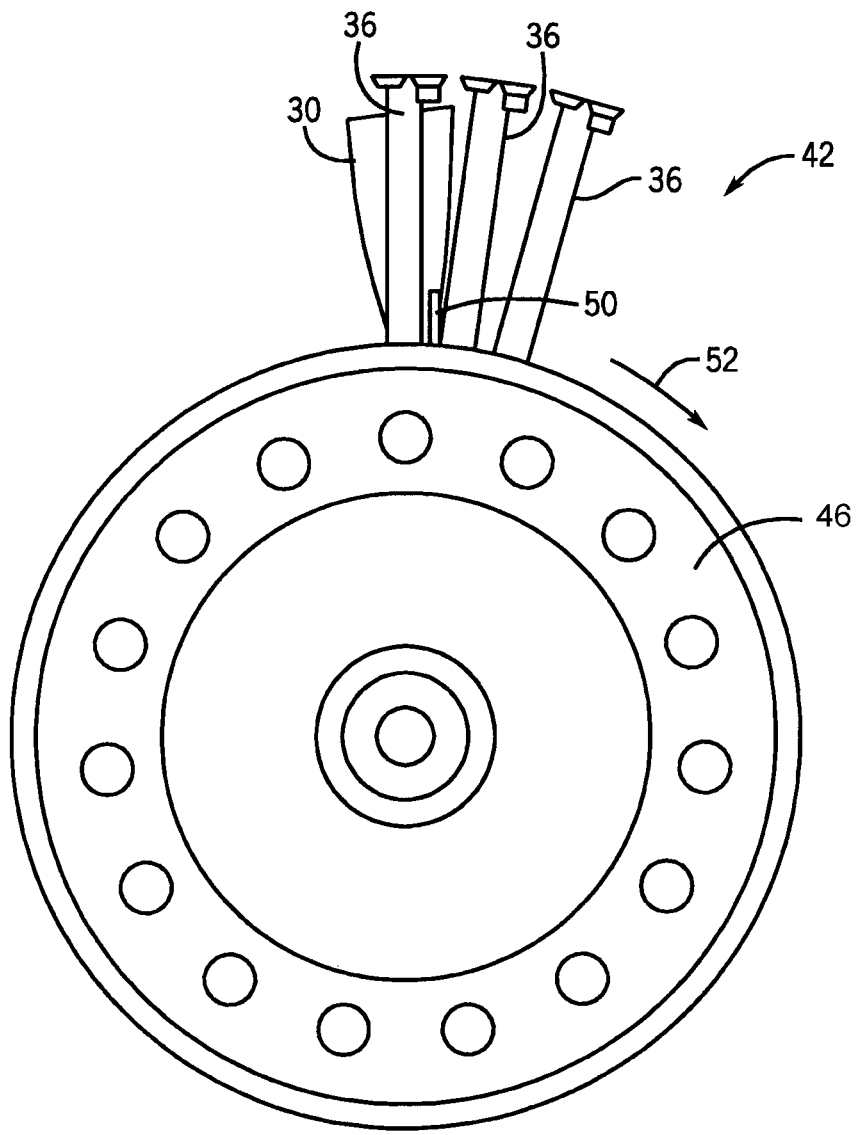
FIG. 4 is a front view of the stage of FIG. 3 with an image recording assembly in accordance with an embodiment of the present invention.

FIG. 4 depicts a front view of a stage 42 of the compressor 18 in accordance with an embodiment of the present invention. For clarity, only one rotor blade 30 and three stator vanes 36 are illustrated in FIG. 4. As shown in FIG. 4, an image recording assembly 50 is secured to the rotor blade 30. As described further below, the image recording assembly 50 may include an image recording device, a light source, a storage device, a power supply, and a coupling mechanism. The image recording assembly 50 may be secured to any portion of the rotor blade 30, and multiple assemblies 50 may be removably coupled along the radial length of the rotor blade 30. For example, as shown in FIG. 4, the image recording assembly 50 may be secured to the rotor blade 30 near the rotor 46. Thus, as the rotor 46 rotates (such as in the direction illustrated by arrow 52), the image recording assembly 50 rotates along the circumference of stator vanes 36. As the image recording assembly 50 rotates, the image recording assembly 50 may record images of the stator vanes 36 in the field of view of the image recording device. Thus, as the image recording assembly 50 rotates 360 degrees around the axis of rotation of the rotor 46, images of all of the circumference of stator vanes 36 may be recorded.

Figure 5:
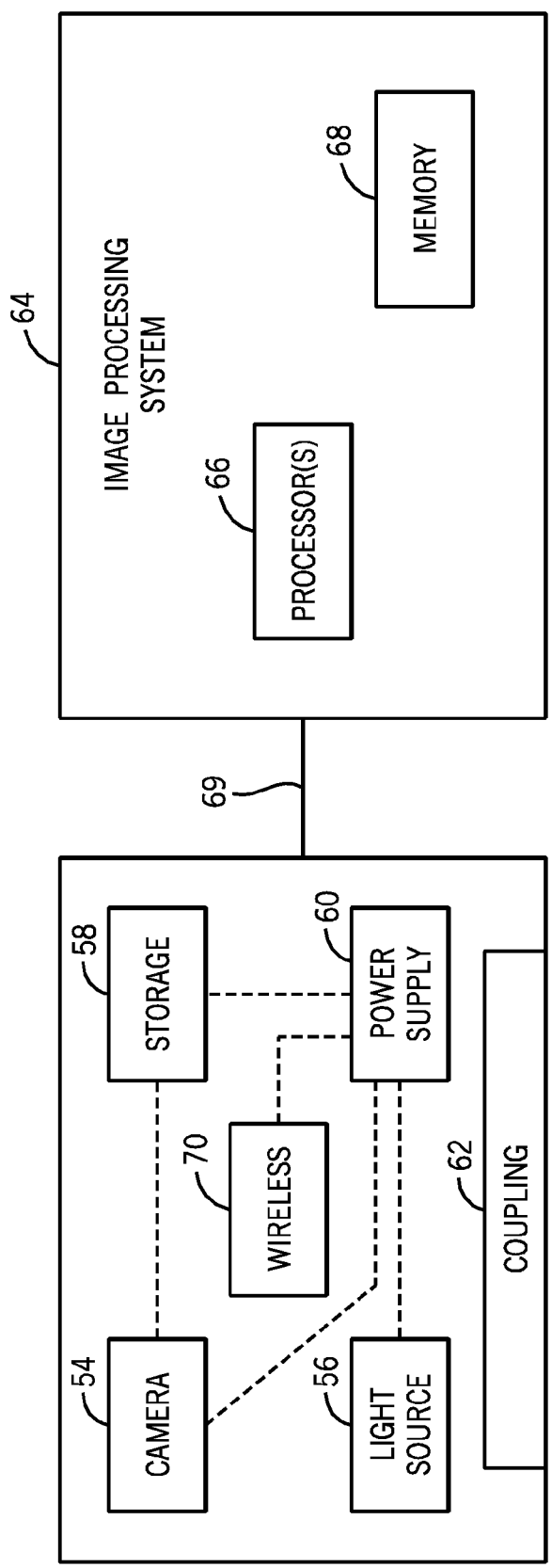
FIG. 5 is a block diagram of an image recording assembly and an imaging processing system in accordance with an embodiment of the present invention.

FIG. 5 depicts a block diagram of the image recording assembly 50 in accordance with an embodiment of the present invention. The image recording assembly 50 may include one or more image recording devices, e.g., cameras 54, one or more light sources 56, one or more storage devices 58 (e.g., non-volatile memory), one or more power supplies 60, and a coupling mechanism 62. In one embodiment, the image recording assembly 50 may have a length of approximately 100 mm, a width of approximately 7.5 mm, a thickness of about 4 mm, and a weight of approximately 50 g. Additionally, FIG. 5 depicts an image processing system 64 (e.g., a computer) having one or more processors 66 and memory 68 (e.g., volatile or non-volatile memory). When removed from the compressor 18, the image recording assembly 54 may be coupled to the image processing system 66 via a cable 69.

The image recording assembly 50 may include one camera oriented towards the stator vanes, or may include multiple cameras oriented in different directions. For example, the cameras 54 may be oriented to inspect the stator vanes of multiple stages on either side or the rotor wheel 32. The number of cameras used to obtain substantially 100% image coverage of a stator vane may be determined from the height of the stator vane and the field of view of the camera. For example, for a stator vane of 27 cm and a field of view diameter of 110 mm, the number of cameras used to provide substantially 100% coverage of the stator vane is approximately 3 (270/110).

The cameras 54 may include an analog camera and/or a digital camera and may receive power from the power supplies 60. In some embodiments, the cameras 54 may record images at a rate of at least about 2 frames-per-second (FPS) and may have a resolution of greater than at least 0.1 MP, 1 MP, 2 MP, or 3 MP. The cameras 54 may include a time mechanism to enable the camera to record images periodically after a specified time interval. Additionally, or alternatively, the cameras 54 may include a trigger mechanism that may be activated by rotation of the rotor blade 30. In some embodiments, the cameras 54 may include an OV9665FF camera and/or an OV2665AF camera manufactured by Supertech Optoelectronics of Taipei, Taiwan.

In some embodiments, the image recording assembly 50 may include a video recording device, so that the image recording assembly 50 records video of the internal components of the compressor 18. In other embodiments, the image recording assembly 50 may include any other image sensing devices, such as infrared, ultrasound, and/or eddy current sensing devices.

The light source 56 may include light emitting diodes (LEDs), fluorescent lights, incandescent lights, or any other suitable light device, and may be oriented to illuminate the stator vanes 36 or any other region capable of image record by the cameras 54. Multiple color light sources may be used, such as blue, green, red, white, or other colors. For example, blue LEDs may be used during a first portion of the inspection and green LEDS may be used during a second portion of the inspection. The storage device 58 may be a non-volatile memory device (e.g., a flash memory device) configured to provide a desired storage capacity and maintain the small size of image recording assembly 50. In one embodiment, the storage device may provide at least 2 GB, 4 GB, 6 GB, or 8 GB of memory.

In some embodiments, a camera 54, a light source 56, and a storage device 56 may form an integrated assembly. In other embodiments a camera 54, a light source 56, and/or a storage device 58 may be individually selected and separately provided in the image recording assembly 50.

The one or more power supplies 60 may include one or more batteries, such as lithium ion, polymer lithium, nickel cadmium, or any other suitable batteries. In one embodiment, the power supplies 60 may include a battery having a capacity of at least about 250 mAh and a voltage of at least about 3 V. The power supplies 60 may be configured to provide for operation for the camera 54, the light source 56, and the storage device 58 for at least the duration of the inspection process.

In one embodiment, the image recording assembly 50 may include three pin-hole cameras (e.g., cameras having CCD or CMOS image sensors, such as an Exmor R back illuminated CMOS image sensor) oriented at 45 degrees, 0 degrees, and 45 degrees relative to the length of the rotor blade. The image recording assembly 50 may include multiple blue SMD LEDs, such that each camera 54 may be encircled by an arrangement of three LEDS. In such an embodiment, the image recording assembly 50 may include an image processor, a memory, a battery, and a field programmable gate array (FPGA) to control and synchronize the subsystems of the assembly 50. Any or all of the above components may be mounted on a flexible printed circuit board (PCB) and disposed inside a housing. The housing may be coupled to the rotor blade using the coupling mechanism 62 described in more detail below. The housing may also include a recessed portion or other feature to enable easier manipulation by a tool.

The coupling mechanism 62 may be configured to provide enough force to secure the image recording assembly 50 against the centrifugal force produced by the rotating blade 30. For example, for an image recording assembly 50 having a weight of about 50 g, an image recording assembly placement of a radial distance of 500 mm from base of the rotor blade 30, and a rotor speed of 1 rpm, the centrifugal force is approximately 0.0003 N. The coupling mechanism 62 may include a magnetic coupling, a clamping mechanism, an adhesive, a pneumatic mechanism, or any other suitable mechanism or combination thereof.

As mentioned above, in some embodiments the coupling mechanism 62 may include a magnetic coupling. The magnetic coupling may be based on permanent magnets, electromagnets, or a pneumatic system. In one embodiment, coupling mechanism 62 may include rare earth permanent magnets with soft iron and brass components. The magnetic field produced by the magnets may be manipulated such that the coupling mechanism has an ON position (the magnetic field is directed outward from the coupling mechanism 62 so the camera assembly 50 can be coupled to a rotor blade) and an OFF position (the magnetic field is concealed inside the coupling mechanism 62 so the camera assembly 50 can be detached from a rotor blade). The manipulation of the magnetic field from the permanent magnets may be performed by a keepers, linear Halbach array, and electro-permanent magnets.

In other embodiments, the coupling mechanism 62 may use an electromagnet having a soft iron core. In such an embodiment, current may be passed through the soft iron core to energize the electromagnet and couple the camera assembly 50 to a rotor blade. In yet other embodiments, a pneumatic system may include an array of micro suction cups and a micro air pump to create a vacuum force and allow the suction cups to couple the image recording assembly 50 to a rotor blade.

In some embodiments, actuation of any of the coupling mechanisms 62 described above may be through a switch included in the image recording assembly 50 and operable by a tool used to insert the image recording assembly 50. For example, in one embodiment an actuation mechanism may include a motor (e.g., a DC or stepper motor) having a shaft attached to the operating mechanism of the coupling mechanism 62 (e.g., the permanent magnet mechanism, a switch for an electromagnet, a switch for a micro air pump, etc.). The actuation mechanism may include a collapsible switch configured to operate the motor, such that the collapsible switch may be collapsed to turn the motor OFF and may be released to turn the motor ON. The collapsible switch may include a spring to bias the switch to the released position. During insertion of the image recording assembly 50, the collapsible switch may be collapsed via a tool (e.g., alligator clips) and then released when the image recording assembly 50 is in position. Such a tool may also include a flexible cable, an image sensor, and an electromagnet, to enable easier viewing and manipulation of the image recording assembly 50 when it is inserted into the compressor 18. The electromagnet may secure the image recording assembly 50 after release of the alligator clips to ensure secure coupling to the rotor blade. In one embodiment, the tool may include borescope tools available from GE Inspection Technologies of Lewistown, Pa.

In some embodiments, the image recording assembly 50 may include a wireless communication device 70 that may be used to transmit images from the cameras 54 and/or storage devices 58 to the image processing system 64. Alternatively, in other embodiments the image recording assembly 50 may be physically connected to the image processing system 64 via the cable 69, when the image recording assembly 50 is removed from the gas turbine engine 12. For example, the image recording assembly 50 may be coupled to the image processing system 64 via a Universal Serial Bus (USB) interface, Firewire interface, eSata interface, or any other suitable interface. The image processing system 64 may also be capable of processing any data received from the image recording assembly 50, such as still images, video, infrared images, ultrasound images, eddy current images, etc.

Figure 6:
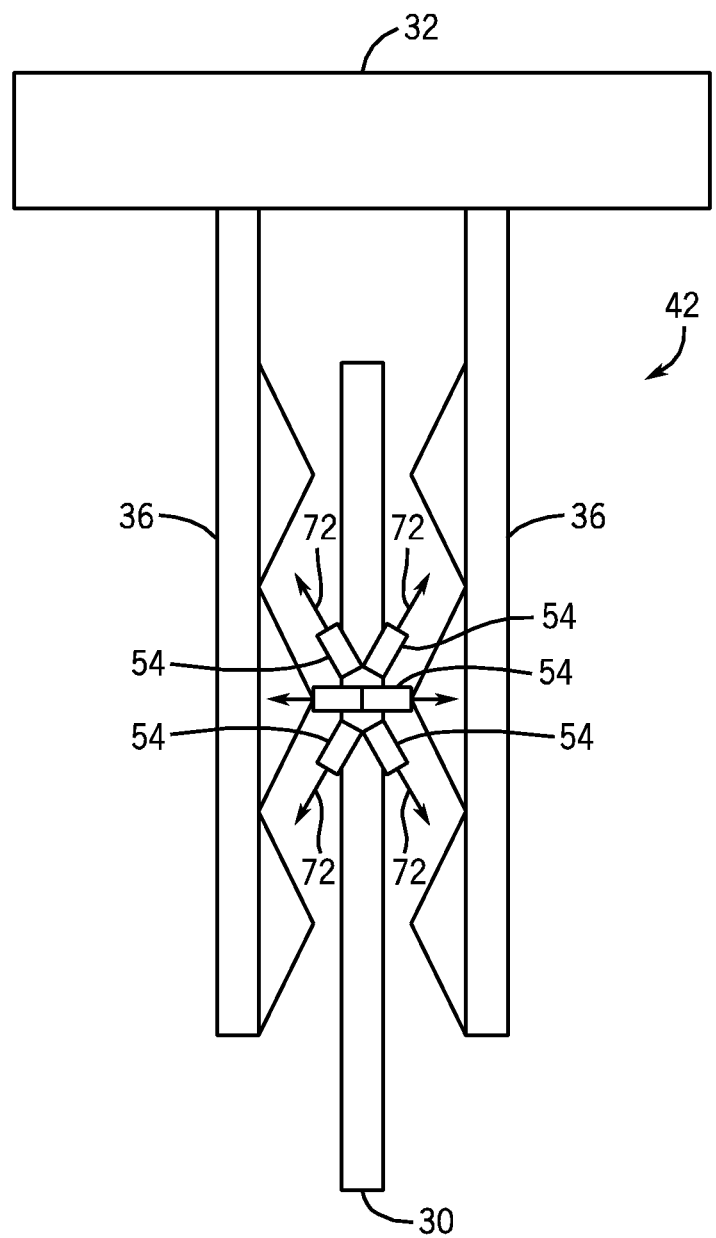
FIG. 6 is a block diagram of a stage of the compressor of the gas turbine engine having multiple cameras in accordance with an embodiment of the present invention.

FIG. 6 depicts a block view of a compressor stage 42 and inspection system in accordance with an embodiment of the present invention. As shown in FIG. 6, a rotor blade 30 is disposed between stator vanes 36 inside the inner wall or surface of the compressor. In the embodiments depicted in FIG. 6, multiple cameras 54, e.g., six cameras, are removably coupled to the rotor blade 30. As noted above, the multiple cameras 54 may be included in a single image recording assembly 50 having multiple cameras or each of the multiple cameras 54 may be included in a respective one of multiple image recording assemblies 50. The cameras 54 may be oriented to provide substantially 100% image coverage of the stator vanes 36 adjacent to the rotor blade 30. For example, as shown in FIG. 6, each camera may be oriented in the directions indicated by arrows 72. As the rotor blade 30 rotates, each camera may continuously or periodically record images of the stator vane 36 viewable from the camera's orientation. Multiple cameras 54 (or image recording assemblies 50) may be removably coupled to each rotor blade 30 of the compressor 18 to provide inspection of all stator vanes 36. Further, in some embodiments, inspection of a circumference of stator vanes 36 may be accomplished by using cameras 54 (and image recording assemblies 50) on multiple rotor blades 30, such that each camera 54 (and image recording assembly 50) records images from a portion of the circumference of stator vanes 36.

Figure 7:
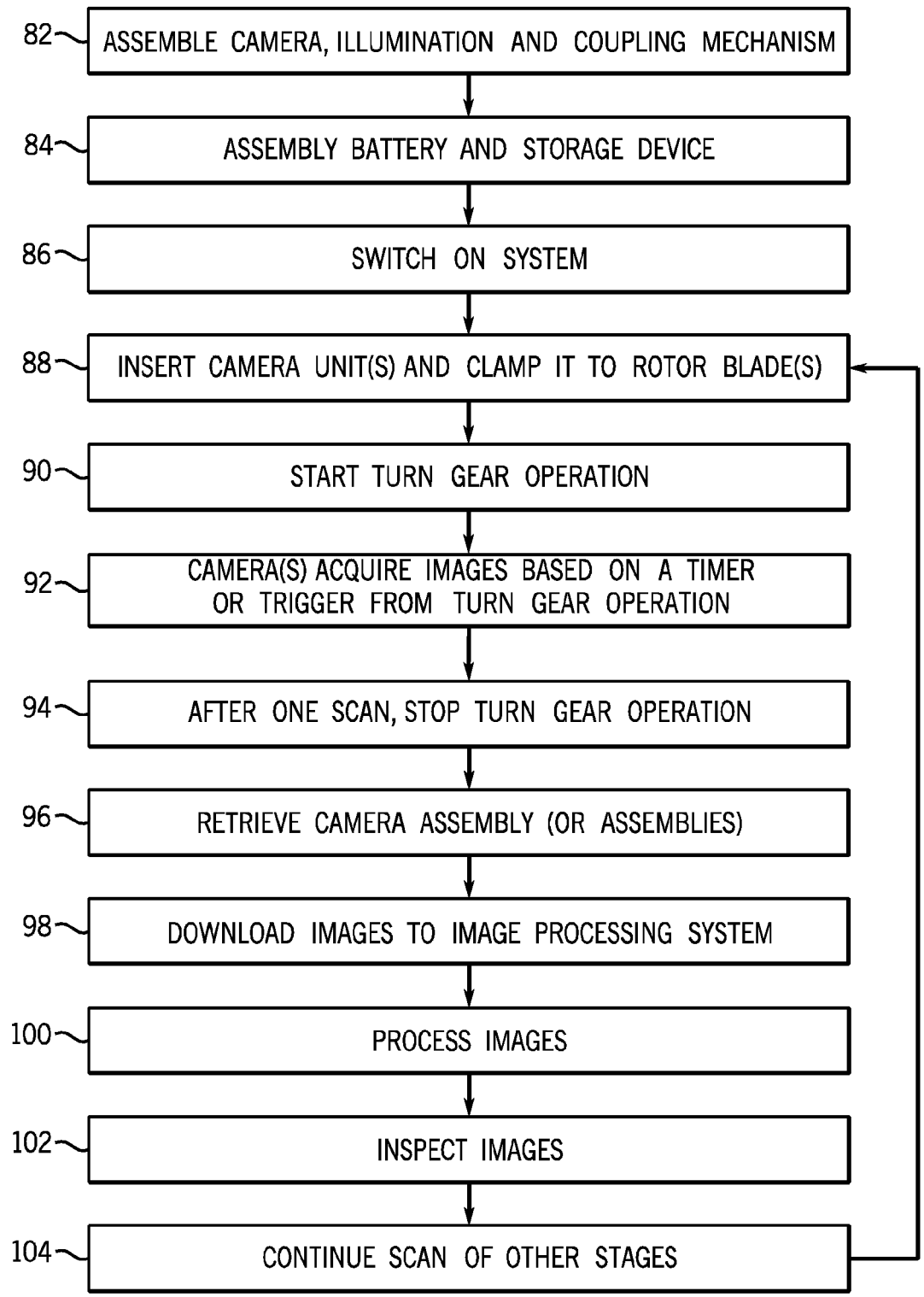
FIG. 7 is a flowchart of a process for inspecting the compressor of a gas turbine engine using an image recording assembly in accordance with an embodiment of the present invention.

FIG. 7 depicts an embodiment of a process 80 for the inspection of the condition of stator vanes 36 of the compressor 18 of the gas turbine engine 12 using the image recording assembly 50 described above. It should be appreciated that the process 80 may be performed during shutdown of the gas turbine engine 12 and compressor 18, and that process 80 may be performed without removal of the housing 34 or disassembly of the compressor 18. Initially, the cameras 54, light sources 56, and coupling mechanism 62 may be assembled (block 82). Next, the power supplies 60 and storage devices 58 may be assembled with the cameras 54, light sources 56, and coupling assembly 62 to form the image recording assembly 50 (block 84). In some embodiments, each time the image recording assembly 50 is used, only the power supplies 60 and/or the storage devices 58 may be replaced (to ensure adequate power and/or storage for the inspection operation). The image recording assembly 50 may be powered on, and the operability of the cameras 54, light sources 56, storage devices 58, and power supplies 60 may be verified (block 86).

The image recording assembly (or assemblies) 50 may be inserted into the compressor 18 of the gas turbine engine 12 and removably coupled to a rotor blade of the compressor 18 (block 88). As described above, in some embodiments the image recording assembly (or assemblies) may be inserted into the compressor 18 through a borescope hole 44. Additional holes may be manufactured in the compressor 18 to allow for insertion of the image recording assembly 50. In some embodiments, multiple image recording assemblies may be inserted into compressor 18 and removably coupled to multiple rotor blades of a rotor. Alternatively, or additionally, multiple image recording assemblies 50 may be inserted into the compressor 18 and removably coupled to rotor blades of different rotor wheels of the compressor 18. The image recording assembly 50 may be inserted into the borescope hole 44 using tools, such as a "gripper," through a work channel attached to the borescope. As described above, such tools may include a flexible cable, alligator clips, and an electromagnet, and the alligator clips may be configured to release a collapsible switch to activate the coupling mechanism 62 of the image recording assembly 50.

After securing the image recording assembly 50 to the rotor blade 30, the turn gear operation of the compressor 18 may be started (block 90). In some embodiments, the turn gear operation may be performed manually such that the shaft and rotors of the compressor 18 are directly or indirectly rotated by a technician. In other embodiments, the turn gear operation may performed automatically by slow turning tools, a motor or other automated rotation of the rotary components of the compressor.

As the rotor wheels of the compressor 18 rotate, the camera(s) 54 of the image recording assembly (or assemblies) 50 records images at periodic or rotational intervals (block 92). The image record may be based on a timer, such that the camera records an image after a duration of time. In other embodiments, the image record may be based on a trigger from the turn gear operation, such that the camera records an image after a specific degree of rotation. In one embodiment, an operator may activate the coupling mechanism 62 by a switch at the borescope arm. Once the image recording assembly 50 gets attached to the rotor blade 30, the "gripper" opens and the operator can retrieve the borescope arm. The opening of the "gripper" triggers the switch which in turn triggers the recording device(s), e.g., cameras 54, of the image recording assembly 50. In another embodiment, a start/stop triggering mechanism may be synchronized with the key-phasor of the turbine 22. At a certain angular position of the key-phasor, the recording device, e.g., cameras 54, may start recording the images. The location of the key-phasor may be determined using a proximity probe. As the key-phasor rotates by a certain angle, the cameras 54 may be triggered wirelessly. The cameras 54 may stop recording as soon as the key-phasor returns back to its original position.

After image record is complete, the turn gear operation may be stopped (block 94). The image record may be complete after one, two, three, four, or more rotations of the image recording assembly around the circumferential arrangement of stator vanes.

The image recording assembly (or assemblies) 50 may then be removed from the gas turbine engine 12 (block 96). As described above, in some embodiments, the image recording assembly (or assemblies) 50 may be removed through the borescope hole 44 of the gas turbine engine 12. As noted above, the image recording assembly (or assemblies) 50 may be removed through the borescope hole 44 through the use of tools, e.g., a "gripper." As described above, such tools may include a flexible cable, alligator clips, and an electromagnet, and the tools may be configured to activate a collapsible switch to deactivate the coupling mechanism 62. The image recording assembly (or assemblies) 50 may be connected to the image processing system 64 and images recorded by the cameras 54 may be downloaded from the storage devices 58 to the image processing system (block 98). For example, the image recording assembly (or assemblies) 50 may be coupled to the image processing system 64 by a cable 69. In other embodiments, the image recording assembly (or assemblies) 50 may include a wireless communication device 70 that may provide for wireless downloading of images to the image processing system 64 (with or without removal of the image recording assembly (or assemblies) 50 from the compressor 18). The image processing system processor 66 may process the images recorded by the cameras 54 to provide for easier interpretation of the images and any wear and defects on the stator vanes shown in such images (block 100). Such image processing may include color channel splitting (e.g., RGB splitting), contrast enhancement, edge detection (e.g., Canny edge detection), magnification, or any other image processing. After processing the images, the images may be inspected (block 102). In some embodiments, the images may be manually inspected by a technician to identify wear and/or defects of the stator vanes or other internal components shown in the images. In other embodiments, the image processing system 64 may automatically inspect the images to identify wear and/or detects, such as by looking for areas having certain attributes Finally, the scan of other stages may continue using the same or additional image recording assemblies 50 (block 104).

Advantageously, the inspection process 80 described above may provide increased coverage area of the inspection and inspection of the interior components of the gas turbine engine 12 without removal of the housing of the compressor 12 or other components. The increased coverage area may increase the probability of detection of wear and/or defects in the stator vanes or other internal components recorded by the image recording assembly. Further, the inspection process 80 may be automated at various tasks, such as image record and image processing. Additionally, the inspection process 80 described above may be less time consuming and easier to perform than other inspection processes, thus increasing productivity and reducing inspection time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   removably coupling an image recording assembly to a rotary component of a compressor of a gas turbine engine such that a plurality of cameras disposed within the image recording assembly are oriented in different directions from each other relative to a length of the rotary component;
   rotating the image recording assembly around a shaft of the gas turbine engine; and
   recording images of stationary components disposed circumferentially around the shaft, without removal of a housing of the compressor.

2. The method of claim 1, comprising storing images in a storage device of the image recording assembly.

3. The method of claim 1, wherein the rotary component comprises a rotor blade.

4. The method of claim 1, wherein the stationary components comprise stator vanes.

5. The method of claim 1, wherein rotating an image recording assembly comprises rotating the shaft of the gas turbine engine.

6. The method of claim 1, wherein recording images of the stationary components comprises recording images using at least one camera of the image recording assembly.

7. The method of claim 1, comprising downloading images from the image recording assembly to an image processing system.

8. The method of claim 1, wherein downloading images comprises downloading images via a wireless communication device of the image recording assembly.

9. The method of claim 8, comprising illuminating the stationary components via a light source of the image recording assembly.

10. The method of claim 1, wherein the plurality of cameras comprise a plurality of pin-hole cameras.

11. A system, comprising:
    an image recording assembly for a compressor of a gas turbine engine, comprising:
       a plurality of cameras for recording images of stator vanes of the compressor as a rotor blade of the compressor rotates; a light source; and a storage device, wherein each camera of the plurality of cameras is oriented in a different direction from each other camera relative to a length of the rotor blade, and;
    a coupling mechanism for coupling the image recording assembly to the rotor blade.

12. The system of claim 11, wherein the light source comprises a light emitting diode.

13. The system of claim 11, wherein the storage device comprises a flash memory device.

14. The system of claim 11, further comprising an image processing system, wherein the image recording assembly further comprises an interface for communication with the image processing system.

15. The system of claim 11, wherein the image recording assembly further comprises a power supply configured to provide power to the plurality of cameras, the light source, the storage device, or any combination thereof.

16. The system of claim 11, wherein the plurality of cameras comprise a plurality of pin-hole cameras.

17. A method, comprising:
    inserting a camera assembly comprising a plurality of cameras into a compressor housing of a gas turbine engine such that each camera of the plurality of cameras is oriented in a different direction from each other camera relative to a length of a rotor blade;
    coupling the camera assembly to the rotor blade; and
    determining defects in an internal component of the compressor from images recorded by the camera assembly.

18. The method of claim 17, comprising removing the camera assembly from the compressor housing of the gas turbine engine.

19. The method of claim 17, wherein inserting the camera assembly comprises inserting the camera assembly through a borescope hole of the compressor housing.

20. The method of claim 17, wherein determining defects comprises determining defects in stator vanes of the compressor from images recorded by the camera assembly.

* * * * *